United States Patent [19]

Nagasawa et al.

[11] Patent Number: 5,624,955

[45] Date of Patent: Apr. 29, 1997

[54] COMPOUNDS THAT ENHANCE THE CONCENTRATION OF GLUTATHIONE IN TISSUES

[75] Inventors: Herbert T. Nagasawa, Richfield; William B. Rathbun, Bloomington; Jonathan F. Cohen, Prior Lake, all of Minn.

[73] Assignee: Regents of the University of Minnesota, Minneapolis, Minn.

[21] Appl. No.: 433,809

[22] Filed: May 3, 1995

[51] Int. Cl.⁶ .................................................... A61K 31/21
[52] U.S. Cl. ........................ 514/513; 558/254; 435/110
[58] Field of Search ......................... 558/254; 514/513; 435/110

[56] References Cited

U.S. PATENT DOCUMENTS 4,868,114   9/1989   Nagasawa et al. .................... 435/112

FOREIGN PATENT DOCUMENTS

| 0332946 | 9/1989 | European Pat. Off. . |
| 0373002 | 6/1990 | European Pat. Off. . |
| 64-26516 | 1/1989 | Japan . |
| WO88/00182 | 1/1988 | WIPO . |
| WO92/00320 | 1/1992 | WIPO . |

OTHER PUBLICATIONS

O. Abe et al., "Synthesis of Mixed Disulfides with Cyanogen Bromide and Its Consequences for Elucidation of Protein Structure", *J. Org. Chem.*, 39, 253–255 (1974).

Anderson et al., "Glutathione Monoesters," *Anal. Biochem.*, 183, 16–20 (1989).

Brick et al., "The Preparation of S–acetylglutathione," *Chemistry and Industry*, 1513–1514 (Dec. 4, 1954).

Chen et al., "Life Span Profiles of Glutathione and Acetaminophen Detoxification," *Drug Metab. Dispos.*, 18, 882–887 (1990).

Chen et al., "Glutathione Ester Corrects the Kidney Glutathione and Cysteine Deficiencies in the Aging Mouse," *The Toxicologist*, 10, Abstract No. 1280, p. 320 (1990).

Datta et al., "Mescaline–Induced Changes of Brain–Cortex Ribosomes," *Biochem. J.*, 117, 961–968 (1970).

Deneke et al., "Regulation of cellular glutathione," *Am. J. Physiol.*, 257, L163–L173 (1989).

(List continued on next page.)

*Primary Examiner*—Robert Gerstl
*Attorney, Agent, or Firm*—Mueting, Raasch, Gebhardt & Schwappach, P.A.

[57] ABSTRACT

A pharmaceutical unit dosage form comprising an amount of a compound of the formula:

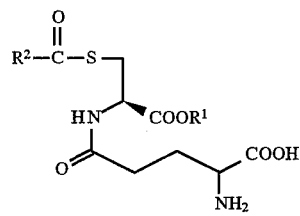

is provided wherein $R^1$ is a $(C_1\text{-}C_{20})$alkyl group, a $(C_6\text{-}C_{12})$ aryl group, or a $C_3\text{-}C_{18}$)cycloalkyl group and $R^2$ is H or a $(C_1\text{-}C_{19})$alkyl group, a $(C_6\text{-}C_{12})$aryl group, a $(C_7\text{-}C_{13})$ arylalkoxy group, a $(C_1\text{-}C_6)$alkyoxy group, a $(C_3\text{-}C_{18})$ cycloalkyl group, a

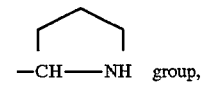

group, or a —$CH(R^3)NH_2$ group wherein $R^3$ is a side chain of a natural amino acid, and the pharmaceutically acceptable salts thereof; in combination with a pharmaceutically acceptable carrier, wherein said amount is effective to increase the concentration of glutathione in tissue.

15 Claims, 1 Drawing Sheet

OTHER PUBLICATIONS

Elberling et al., "N–Phthaloyl–L–Glutamic Anhydride (2–Phthalimidoglutaric Anhydride)," *Org. Prep. Proced. Int.*, 11, 67–70 (1978).

Fariss et al., "High–Performance Liquid Chomatography of Thiols and Disulfides: Dinitrophenol Derivatives," *Methods in Enzymology*, 143, 101–109 (1987).

Gander et al., "Bovine Lens γ–Glutamylcysteine Synthetase; Inhibition by Glutathione and Adenine Nucleotides," *Eur. J. Biochem.*, 133, 635–640 (1983).

Hattori et al., "Effect of γ–glutamyl–cysteinyl ethyl ester on lens glutathione level and diabetic cataract formation in rats," *Chem. Abs.*, 112, Abstract No. 112:172260g, p. 76 (1990).

Hazelton et al., "Glutathione Contents of Tissues in the Aging Mouse," *Biochem J.*, 188, 25–30 (1980).

Holleschau et al., "Procedures for Augmenting Glutathione in Cultured Rabbit Lenses," *Lens Res.*, 3, 107–118 (1986).

H. Ishii et al., "Mechanism of Growth Stimulation of L1210 Cells by 2–Mercaptoethanol *in Vitro*", *J. Biol. Chem.*, 256, 12387–12392 (Dec. 10, 1981).

Jocelyn, "Oxidation of Thiols" in *Biochemistry of the SH Group;* Academic Press: London; Chapter 4, pp. 95–115 (1972).

Kahns et al., "Prodrugs as drug delivery systems. 107. Synthesis and chemical and enzymatic hydrolysis kinetics of various mono–and diester prodrugs of N–acetylcysteine," *Int. J. Pharm.*, 62, 193–205 (1990).

Katayama et al., "Protective agents against lens protein aggregation induced by UV oxidation," *Chem. Abs.*, 108, Abstract No. 108:218260e, p. 259 (1988).

Kielly et al., "Glutathione Thioesterase," *J. Biol. Chem.*, 206, 327–333 (Jan. 1954).

Kinsey et al., "Studies on the Crystalline Lens," *Arch. Ophthalmology*, 44, 370–380 (1950).

Kitahara et al., "Preparation of gamma–L–glutamyl–L–cysteine ethyl ester for increasing tissue glutathione levels", *Chem. Abs.*, 109, Abstract No. 109:110912a, p. 676 (1988).

Lam, "Glutathione Generators in Cancer Chemoprevention", Abstract of Grant No. 21985 sponsored by National Institutes of Health, obtained from Dialog database Federal Research in Progress.

Levy et al., "Transport of glutathione diethyl ester into human cells," *Proc. Nat'l. Acad. Sci. USA*, 90, 9171–9175 (Oct. 1993).

Magnan et al., "Drug Latentiation by γ–Glutamyl Transpeptidase," *J. Med. Chem.*, 1018–1021 (Sep. 1982).

Murray et al., "Conditions for maximizing and inhibiting synthesis of glutathione in cultured rat lenses: an application of HPLC with radioisotope detection," *Current Eye Research*, 9, 55–63 (1990).

Nagasawa et al., "2–Substituted Thiazolidine–4(R)–carboxylic Acids as Prodrugs of L–Cysteine, Protection of Mice against Acetaminophen Hepatoxicity," *J. Med. Chem.*, 27, 591–596 (1984).

Nagasawa et al., "Differentiation of α–from γ–Glutamyl Dipeptides by Chemical Ionization Mass Spectrometry," *Biomedical Mass Spectrometry*, 9, 252–256 (1982).

Nagasawa, "Medicinal Chemistry Aspects of Alcoholism", Abstract of Grant No. 40467 sponsored by the Department of Veterans Affairs, obtained from Dialog database Federal Research in Progress.

Ohtsu et al., "Anticataractogenic Property of γ–Glutamylcysteine Ethyl Ester in an Animal Model of Cataract," *Ophthalmic Res.*, 23, 51–58 (1991).

O'Neil, "Reverse Phase Flash Chromatography: A Convenient Method for the Large Scale Separation of Polar Compounds," *SYNLETT*, 661–662 (Sep. 1991).

Pau et al., "Glutathione Levels in Human Lens: Regional Distribution in Different Forms of Cataract," *Exp. Eye Res.*, 50, 17–20 (1990).

Racker, "The Mechanism of Action of Glyoxalase," *J. Biol. Chem.*, 190, 685–696 (Jun. 1951).

Rathbun, "Activity of glutathione synthesis enzymes in the rhesus monkey lens related to age: a model for the human lens," *Current Eye Research*, 5, 161–166 (1986).

Rathbun et al., "Activity Loss of Glutathione Synthesis Enzymes Associated with Human Subcapsular Cataract," *Invest. Ophthal. Vis. Sci.*, 34, 2049–2054 (May 1993).

Rathbun et al., "Age–related Cysteine Uptake as Rate–limiting in Glutathione Synthesis and Glutathione Half–life in the Cultured Human Lens," *Exp. Eye Res.*, 53, 205–212 (1991).

Rathbun et al., "β–Aminoisobutyrate in the Coupled Enzymic Assay of Bovine Lens γ–Glutamylcysteine Synthetase," *Anal. Biochem.*, 54, 153–160 (1973).

Rathbun, "Biochemistry of the Lens and Cataractogenesis: Current Concepts," *Veterinary Clinics of North America: Small Animal Practice*, 10, 377–398 (May 1980).

Rathbun et al., "The effects of age on glutathione synthesis enzymes in lenses of Old World simians and prosimians," *Current Eye Research*, 11, 601–607 (1992).

Rathbun et al., "Estimation of Enzymatically Produced Orthophosphate in the Presence of Cysteine and Adenosine Triphosphate," *Anal. Biochem.*, 28, 436–445 (1969).

Rathbun, "γ–Glutamyl–Cysteine Synthetase from Bovine Lens; I. Purification and Properties," *Arch. Biochem. Biophys.*, 122, 62–72 (Oct. 1967).

Rathbun, "γ–Glutamyl–Cysteine Synthetase from Bovine Lens; II. Cysteine Analogue Studies," *Arch. Biochem. Biophys.*, 122, 73–83 (Oct. 1967).

Rathbun, "Glutathione in Ocular Tissues," Offprint from *Glutathione: Chemical, Biochemical, and Medical Aspects, Part B;* D. Dolphin et al., Eds.; John Wiley & Sons; pp. 467–510 (1989).

Rathbun, "Glutathione Synthesis in Evolution: An Achilles'Heel of Human and Other Old World Simian Lenses," *Ophthalmic Res.*, 18, 236–242 (1986).

Rathbun, "Lenticular glutathione synthesis: rate–limiting factors in its regulation and decline," *Current Eye Research*, 3, 101–108 (1984).

Rathbun et al., "Purification and Properties of Glutathione Synthetase from Bovine Lens," *Exp. Eye Res.*, 24, 145–158 (1977).

Rathbun,"Glutathione Metabolism in Ocular Tissues", Abstract of Grant No. 5R01EY01197–21 sponsored by the National Eye Institute, obtained from Dialog database Federal Research in Progress.

Reddy et al., "Evidence for lens oxoprolinase, an enzyme of the gamma–glutamyl cycle", *Invest. Opthal.*, 14, 228–232 (1975).

*Remington's Pharmaceutical Sciences (17th Ed.);* A.R. Gennaro, Ed.; Mach Publishing: Easton, PA (1985)—Title page, copyright page and Table of Contents.

Roberts et al., "Mechanisms of Chemoprotection by RibCys, a Thiazolidine Prodrug of L–Cysteine," *Med. Chem. Res.*, 1, 213–219 (1991).

Roberts et al., "Prodrugs of L–Cysteine as Protective Agents against Acetaminophen–Induced Hepatoxicity. 2–(Polyhydroxyalkyl)–and 2–(Polyacetoxyalkyl)thiazolidine–4(R)–carboxylic Acids," *J. Med. Chem.*, 30, 1891–1896 (1987).

Sethna et al., "Glutathione synthetase of bovine lens: anomalies of the enzyme–catalzyed formation of ophthalmic acid," *Current Eye Research*, 3, 923–928 (1984).

Sethna et al., "Activity of glutathione synthesis enzymes in human lens related to age," *Current Eye Research*, 2, 735–742 (1982/1983).

Sheehan et al., "A New Synthesis of Cysteinyl Peptides," *J. Am. Chem.*, 80, 1158–1164 (Mar. 5, 1958).

Sippel, "The relationship of rat lens respiration to oxygen concentration and pH," *Investigative Ophthalmology*, 385–389 (Jun. 1962).

Stipanuk et al., "Cysteine Concentration Regulates Cysteine Metabolism to Glutathione, Sulfate and Taurine in Rat Hepatocytes," *J. Nutr.*, 122, 420–427 (1992).

Threadgill et al., "Synthesis of Peptides Containing S–(N–Alkylacarbamoyl)cysteine Residues, Metabolites of N–Alkylformamides in Rodents and in Humans," *J. Org. Chem.*, 54, 2940–2949 (1989).

Uotila, "Thioesters of Glutathione," *Methods of Enzymology*, 77, 424–430 (1981).

Van Buskirk et al., "Bovine Lenticular γ–Glutamylcysteine Synthetase: Reaction Sequence," *Eur. J. Biochem.*, 85, 589–597 (1978).

Williamson et al., "Stimulation of hepatic glutathione formation by administration of L–2–oxothiazolidine–4–carboxylate, a 5–oxo–L–prolinase substrate," *Proc. Natl. Acad. Sci. USA*, 78, 936–939 (Feb. 1981).

Solsten, ALS., S.ymp. Ser. (1990) 420, 92–122.

COMPOUNDS THAT ENHANCE THE CONCENTRATION OF GLUTATHIONE IN TISSUES

BACKGROUND OF THE INVENTION

Cataract is the only known disease of the lens. Cataracts are opacities in the lens of the eye that result in a change in refractive index. They are characterized by decreased levels of some of the proteins of the lens. In addition, non-reversible cataracts are characterized by very low levels of the sulfur-containing tripeptide glutathione, γ-L-glutamyl-L-cysteinylglycine ($HOOCCH(NH_2)CH_2CH_2C(O)NHCH(CH_2SH)C(O)NHCH_2COOH$). See, W. B. Rathbun, Chapter 14 in *Glutathione: Chemical, Biochemical, and Medical Aspects*, Vol. III, Part B of the series *Coenzymes and Cofactors*; D. Dolphin et al., Eds.; Wiley, New York; (1989) pp. 467–510. Glutathione is widely regarded as a major and essential antioxidant for protection of the lens from exogenous noxious agents such as ultraviolet radiation, free radicals, and various toxic compounds of xenobiotic origin.

Biosynthesis of glutathione (GSH) involves two sequential reactions catalyzed by the enzymes γ-glutamylcysteine synthetase and glutathione synthetase (GSH-synthetase) using the three precursor amino acids L-glutamic acid, L-cysteine, and glycine, as shown below:

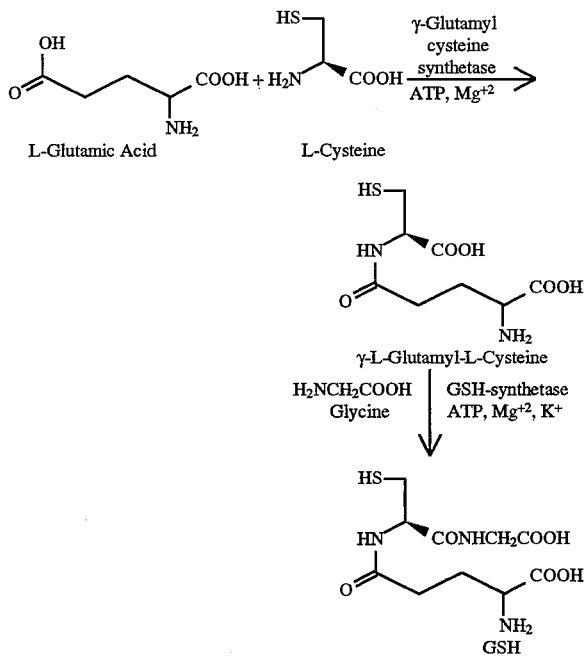

All substrate-level reactants occur at near enzyme-saturating concentrations in vivo with one exception. This exception is L-cysteine whose cellular concentration is exceedingly low. Therefore, the first reaction in which L-cysteine is required, i.e., the synthesis of γ-L-glutamyl-L-cysteine, is the rate-limiting step of glutathione biosynthesis. Thus, the availability of intracellular L-cysteine is a critical factor in the overall biosynthesis of GSH.

The concentration of GSH in lenses and other tissues generally decreases with age. This is related, at least in part, to the progressive loss of γ-glutamylcysteine synthetase activity and L-cysteine transport capability. Furthermore, the degree of loss of both the biosynthetic enzymes γ-glutamylcysteine synthetase and glutathione synthetase has been shown to be directly proportional to the degree of opacity in human subcapsular cataract. See, for example, W. B. Rathbun and D. L. Murray, *Exp. Eye Res.*, 53, 205–212 (1991); S. S. Sethna and W. B. Rathbun et al., *Curr. Eye Res.*, 2, 735–742 (1983); and W. B. Rathbun et al., *Invest. Ophthal. Vis. Sci.*, 34, 2049–2054 (1993). The concentration of GSH can also be very low in diabetic lenses.

Thus, current efforts are directed at increasing the levels of GSH in the lenses of the aging and diabetic in an attempt to eliminate a key factor for cataractogenesis, as well as increasing GSH levels in other tissues to inhibit oxidative stress and tissue degradation. This has been done by implementing the following therapeutic strategies: (a) providing L-cysteine, the key precursor amino acid; (b) providing the dipeptide precursor γ-L-glutamyl-L-cysteine, thereby by-passing the first biosynthetic step involved in GSH biosynthesis; or (c) providing GSH itself and bypassing both synthetic steps. See, for example, S. M. Deneke et al., *Am. J. Physiol.*, 257, L 163-L 173 (1989). However, exogenously administered L-cysteine and/or GSH are not effective in raising cellular GSH levels due to their rapid catabolism and/or poor transport into the cells.

The cysteine prodrugs, L-2-oxothiazolidine-4-carboxylic acid, and ribosecysteine, the latter a thiazolidine-4-carboxylic acid derived from the condensation of D-ribose with L-cysteine, are effective cysteine delivery systems that raise cellular glutathione levels. See, J. M. Williamson et al., *Proc. Natl. Acad. Sci., USA*, 78, 936–939 (1981); J. C. Roberts and H. T. Nagasawa et al., *J. Med. Chem.*, 30, 1891–1896 (1987); and A. M. Holleschau and W. B. Rathbun et al., *Lens Res.*, 3, 107–117 (1986). These thiazolidine-4-carboxylic acids have been claimed to delay cataract formation in rats fed an elevated sugar diet (W. H. Garner et al., Allergan, Inc., Eur. Pat. Appln. No. EP 373,002, Jun. 13, 1990). However, L-2-oxothiazolidine-4-carboxylic acid requires pyroglutamyl hydrolase (5-oxoprolinase) to release cysteine. This enzyme is low in lens (V. N. Reddy, et al., *Invest. Opthal.*, 14, 228–232 (1975)). Furthermore, ribose-cysteine dissociates non-enzymatically in aqueous solutions (J. C. Roberts et al., *Med. Chem. Rev.*, 1, 213–219 (1991)) thereby rendering it difficult to prepare stable aqueous pharmaceutical dosage forms.

The dipeptide prodrug of glutathione, γ-L-glutamyl-L-cysteine monomethyl ester (methyl ester group on the cysteinyl moiety), has been shown to raise cellular GSI-I levels by effectively by-passing the γ-glutamylcysteine synthetase-catalyzed reaction. See, A. Ohtsu et al., Japanese Patent No. 64-26516 (1989); and A. Ohtsu et al., *Ophthalmic Res.*, 23, 51–58 (1991). The GSH prodrug glutathione monoethyl ester (ethyl ester group on the terminal glycine) is readily transported across cell membranes and hydrolyzed by intracellular esterases to release the GSH directly. Furthermore, a series of methyl, ethyl, n-propyl, and isopropyl mono esters of GSH as well as methyl, ethyl, n-propyl, and n-butyl diesters of GSH have also been prepared as lipophilic prodrug forms of GSH. See, M. E. Anderson et al., *Anal. Biochem.*, 183, 16–20 (1989). However, aqueous pharmaceutical formulations of these mono and diesters are unstable and rapidly deteriorate over time. Thus, what is needed are new, stable prodrug forms capable of increasing the cellular concentration of glutathione, which is beneficial, for example, in the treatment and/or prevention of cataracts and oxidative stress and tissue degradation.

SUMMARY OF THE INVENTION

The present invention provides a novel compound and pharmaceutical unit dosage form comprising an amount of the compound of the formula:

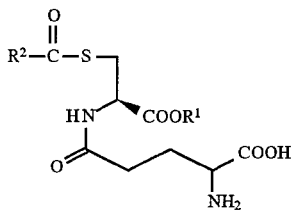

wherein $R^1$ is a $(C_1\text{-}C_{20})$alkyl group, a $(C_6\text{-}C_{12})$aryl group, or a $(C_3\text{-}C_{18})$cycloalkyl group and $R^2$ is H or a $(C_1\text{-}C_{19})$alkyl group, a $(C_6\text{-}C_{12})$aryl group, a $(C_7\text{-}C_{13})$arylalkoxy group, a $(C_1\text{-}C_6)$alkoxy group, a $(C_3\text{-}C_{18})$cycloalkyl group, a

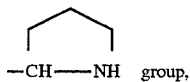

or a $-\text{CH}(R^3)\text{NH}_2$ group wherein $R^3$ is a side chain of a natural amino acid, and the pharmaceutically acceptable salts thereof. In either $R^1$ or $R^2$, the alkyl group can be branched or unbranched and it can contain 0–3 double bonds. In $R^2$, the alkyl group can be either unsubstituted or substituted with hydroxy, amino, or oxo groups. In $R^2$, the aryl group can include heteroaromatic groups, i.e., aryl groups containing a heteroatom (e.g., N, S, or O). Furthermore, in $R^2$, the aryl group can be substituted or unsubstituted. Preferably, $R^1$ is a $(C_1\text{-}C_6)$alkyl group and $R^2$ is a $(C_1\text{-}C_3)$alkyl group. More preferably, $R^1$ is an ethyl group and $R^2$ is a methyl group. The pharmaceutical unit dosage form includes an amount of the compound effective to increase the concentration of glutathione in tissue and a pharmaceutically acceptable carrier.

The present invention also provides a method of enhancing of the concentration of glutathione in lenses and other tissues comprising administering an effective amount of the compound described above. Further, the present invention provides a method of protecting sulfhydryl groups in a peptidyl compound and a method of preparing a γ-glutamylcysteine compound.

DETAILED DESCRIPTION OF THE INVENTION

Figure 1:
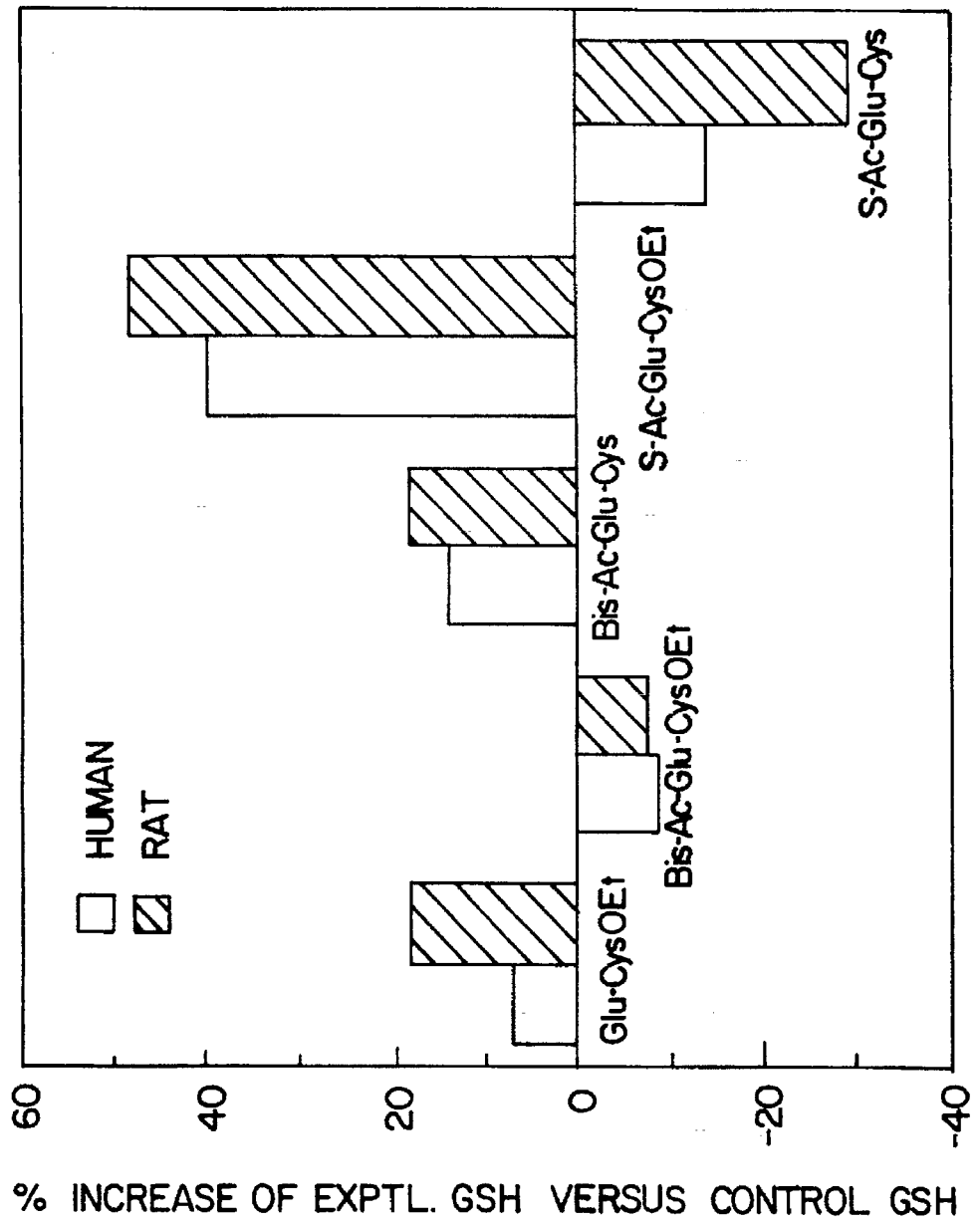
FIGURE 1 is a graph of the percentage increase in the level of glutathione in human and rat lenses as a result of incubation with the identified compounds.

The present application relates to a process for the preparation of generally stable derivatives of glutathione prodrugs, to derivatives obtained from this process, and to pharmaceutical preparations containing these derivatives. These derivatives have therapeutic value for human afflictions, particularly for preventing or treating cataracts associated with aging ("senile cataract"), diabetes, or galactosemia. These derivatives also have therapeutic value for the inhibition of oxidative stress and tissue degradation. Aqueous formulations of these derivatives are generally stable in the absence of phosphate ions.

Age-related factors presumably render tissues, such as lenses, more susceptible to oxidative stress and cataractogenesis. For example, lenses from Old World primates and humans have exhibited 35- to 100-fold less γ-glutamylcysteine synthetase activities than those from various non-primates, and marked age-related decreases in GSH levels in human lenses have been reported. Low levels of GSH have also been associated with oxidative stress and tissue degradation in other tissues. For example, studies have shown that tissue GSH levels in the liver, kidney, spleen, heart, lung, and blood are depressed in aged mice. Such oxidative stress and loss of GSH in tissues may also be caused by alcoholism or AIDS.

Several methods are known for the stabilization of GSH and its prodrugs. One such method involves the selective acylation of the sulfhydryl (—SH) group. The sulfhydryl group is a highly reactive biological nucleophile and is chemically very susceptible to oxidation by a variety of oxidants, including oxygen in the air. It is especially susceptible to oxidation in aqueous solution in the presence of trace amounts of dissolved oxygen and heavy metal cations.

One method by which the glutathione sulfhydryl group is protected is described in International Publication WO 92/00320 (published Jan. 9, 1992). This method involves the reaction between glutathione and an acyl chloride or a carboxylic acid anhydride in trifluoroacetic acid. Other methods involve enzymatic reactions or reactions of glutathione with thioacetic acid, thiopropionic acid, thiobutyric acid, succinic anhydride, or with S-acylated thioglycolic acids. See, W. W. Kieley and L. B. Bradley, *J. Biol. Chem.*, 206, 327–333 (1954); L. Uotila, *Methods Enzymol.*, 77, 424–430 (1981); and E. Racker, *J. Biol. Chem.*, 190, 685 (1951). The first method is not compatible with chiral C-terminal peptide prodrugs because the C-terminal amino acid is racemized by this procedure resulting in biologically inactive products. The enzymatic methods are not generally applicable for large industrial applications or applicable to peptide prodrugs other than glutathione.

The compounds of the present invention are of the general formula:

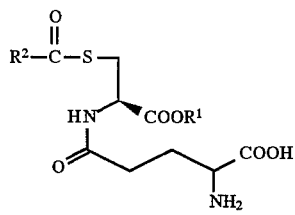

wherein $R^1$ is a $(C_1\text{-}C_{20})$alkyl group, a $(C_6\text{-}C_{12})$aryl group, or a $(C_3\text{-}C_{18})$cycloalkyl group and $R^2$ is H or a $(C_1\text{-}C_{19})$alkyl group, a $(C_6\text{-}C_{12})$aryl group, a $(C_7\text{-}C_{13})$arylalkoxy group, a $(C_1\text{-}C_6)$alkoxy group, a $(C_3\text{-}C_{18})$cycloalkyl group, a

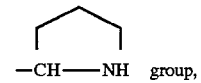

or a $-\text{CH}(R^3)\text{NH}_2$ group wherein $R^3$ is a side chain of a natural amino acid. Natural amino acids include alanine, aspartic acid, cysteine, glutamic acid, phenylalanine, glycine, histidine, isoleucine, lysine, leucine, methionine, asparagine, proline, glutamine, arginine, serine, threonine, valine, tryptophan, and tyrosine. In either $R^1$ or $R^2$, the alkyl group can be branched or unbranched and it can contain 0–3 double bonds. In $R^2$, the alkyl group can be either unsubstituted or substituted with hydroxy, amino, or oxo groups.

In $R^2$, the aryl group can include heteroaromatic groups, i.e., aryl groups containing a heteroatom (e.g., N, S, or O). Furthermore, in $R^2$, the aryl group can be substituted or unsubstituted. If substituted, the aryl group is substituted with any group that does not interfere in the enhancement of the glutathione concentration. Examples of such substituents include, but are not limited to, alkyl, alkoxy, amino, ($C_1$-$C_2$)alkylamino, ($C_1$-$C_2$)acylamino, chloro. Substituents that render the group toxic are not desired, e.g., I, Br, and $NO_2$.

These compounds are generally stable until bioactivated in vivo by esterases to uncover the sulfydryl group of the cysteinyl moiety. In this context, a stable compound is one that does not air oxidize to the disulfide or other oxides of sulfur. Moreover, the sulfhydryl protecting groups (—C(O)—$R^2$) must be biologically compatible once hydrolyzed by tissue esterases. Therefore, the sulfhydryl protecting groups of the present invention take the form of acyl thioesters that are biologically compatible and are hydrolyzable by tissue esterases to liberate the free sulfhydryl group. Examples of biologically compatible acyl groups on the sulfur include, but are not limited to: benzoyl

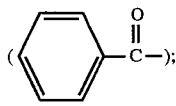

pivaloyl

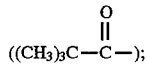

the endogenous even numbered ($C_2$-$C_{18}$)alkanoyl groups, such as acetyl up to stearoyl

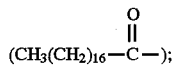

lactoyl

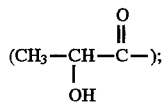

pyruvyl

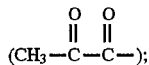

α-ketobutyroyl

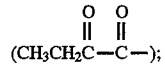

α-hydroxybutyroyl

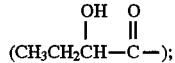

acetoacetyl

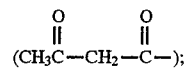

succinyl

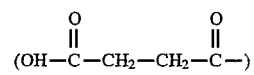

and α-aminoacyl

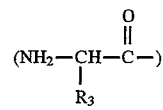

wherein $R_3$ is a side chain of a natural amino acid. Preferably, $R^1$ is a ($C_1$-$C_6$)alkyl group and $R^2$ is a ($C_1$-$C_3$) alkyl group. More preferably, $R^1$ is an ethyl group and $R^2$ is a methyl group.

For certain embodiments, the present invention includes a compound of the formula

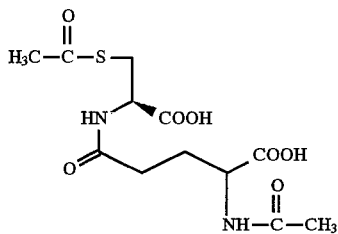

and the pharmaceutically acceptable salts thereof.

In clinical practice, these compounds, and the pharmaceutically acceptable salts thereof, can be administered in the form of a pharmaceutical unit dosage form comprising the active ingredient in combination with a pharmaceutically acceptable carrier, which can be a solid, semi-solid, or liquid diluent. A unit dosage of the compound can also be administered without a carrier material. Examples of pharmaceutical preparations include, but are not limited to, tablets, capsules, aqueous solutions, suspensions, liposomes, and other slow-releasing formulations, as well as transdermal delivery forms. Typically, the unit dosage form includes about 0.001–99% of the active substance.

The compounds can be delivered by any suitable means, e.g., topically, orally, parenterally. Preferably, they are delivered topically in any common ocular formulation comprising a solution, gel, ointment, suspension, or the like. Preferably, the delivery form is liquid. Standard pharmaceutical carriers for topical, oral, or parenteral compositions may be used, many of which are described in *Remington's Pharmaceutical Sciences*, Mack Publishing Co., Easton, Pa.

For example, for oral administration, suitable pharmaceutical carriers can include mannitol, lactose, starch, magnesium stearate, talcum, glucose, and magnesium carbonate. Oral compositions can be in the form of tablets, capsules, powders, solutions, suspensions, sustained release formulations, and the like. A typical tablet or capsule can contain 40–99% lactose, 1–2% magnesium stearate, and 10–20% cornstarch, along with the active substance (preferably about 0.001–20%).

For parenteral administration, suitable pharmaceutical carriers can include water, saline, dextrose, Hank's solution, Ringer's solution, glycerol, and the like. Parenteral compositions can be in the form of suspensions, solutions, emulsions, and the like. Parenteral administration is usually by injection which can be subcutaneous, intramuscular, or intravenous.

As stated above, preferably the compounds of the present invention are administered in a composition for topical application. Such compositions contain about 0.001–5% of the active substance. For example, a typical eye drop solution can contain about 0.5% hydroxypropyl methyl cellulose, 0.1% dextran, 0.2% glycerin, boric acid, potassium chloride, sodium borate, sodium chloride, in addition to the active substance. A typical ocular cream formulation can contain up to about 98% water, about 1–2% polyvinyl alcohol, about 0–10% nonionic surfactant, about 0–10% mineral oil, about 0–5% pharmaceutical adjuvants, about 0.5% chlorobutanol, and about 0.9% sodium chloride, in addition to the active substance (preferably about 0.001–5%, and more preferably about 0.001–0.1%). A typical ocular ointment formulation can contain about 40–94% white petrolatum, about 5–20% mineral oil, about 1–15% glycol solvent, about 0–10% surfactant, and about 0–10% stabilizer, in addition to the active substance (preferably about 0.001–5%, and more preferably about 0.05–5%).

The amount of the compounds of the present invention to be administered and the frequency of administration to a given mammal, preferably a human patient, will depend on a variety of variables related to the patient's age and physical condition, for example. These dosages can be determined empirically by the art worker using models such as those discussed herein below. It is anticipated, however, that treatment may include an ocular or systemic formulation or dosage containing about 0.01–100 mg per day per kilogram of a patient's body mass. Administration can be once or several times daily depending on the concentration of the formulation being administered, the method of delivery, and the patient's response to therapy.

The method of the present invention protects the sulfhydryl groups of peptidyl compounds by converting them to acyl thioesters that are biologically compatible and capable of being hydrolyzed by non-specific and/or specific tissue esterases to liberate the free —SH group. The method also involves the use of a 2-substituted-thiazolidine-4-carboxylate as the sulfhydryl-protected L-cysteine for coupling with the synthon, phthaloyl-L-glutamic anhydride. This is followed by sequential removal of the phthaloyl protective group and deprotection at sulfur to uncover the sulfhydryl group for subsequent selective S-acylation with minimal N-acetylation. Specific application of this method is shown below in Scheme 1, wherein the cysteine sulfhydryl group is protected as a thiazolidine ring system, which is then followed by condensation of the thiazolidine-4-carboxylic acid with phthaloyl-L-glutamic anhydride, deblocking of the phthaloyl group, cleavage of the thiazolidine ring, and finally selectively S-acylating the mercapto functional group, without acylating the amino group, using multiple applications of $R^2$-C(O)-SH at low temperatures. The low temperatures reduces the amount of N-acylation that occurs.

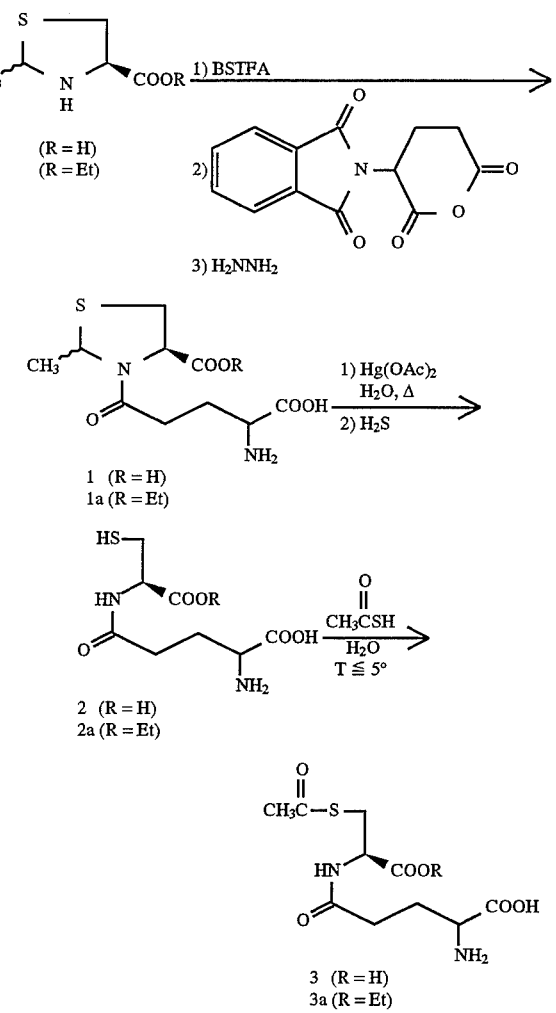

More specifically, 2(R,S)-methylthiazolidine-4(R)-carboxylic acid (or its ethyl ester) is combined with bis-(trimethylsilyl)trifluoroacetamide (BSTFA) in a dry solvent, e.g., $CH_3CN$, and an inert atmosphere, e.g., a $N_2$ atmosphere, with heating under reflux for about 1–2 hours. After cooling to room temperature, N-phthaloyl-L-glutamic anhydride is added, followed by a dry solvent, e.g., $CH_3CN$. After the reaction is complete (typically about 24–48 hours) at no greater than room temperature (25°–30° C.) the solvent is removed, by evaporation, for example. Preferably, this occurs at a temperature below about 40° C. To the resultant product is added $NH_2NH_2 \cdot H_2O$ in an aqueous solvent, e.g., 50% $CH_3OH$, which is allowed to react at room temperature until the reaction is complete (typically about 24 hours). The solvent is then removed, by evaporation, for example, and the desired product [3-(γ-L-glutamyl)-2(R,S)-methylthiazolidine-4(R)-carboxylic acid or its ethyl ester] separated from phthalhydrazide. This material is then combined with mercuric acetate, mercuric chloride, or any soluble divalent mercury salt, in $H_2O$ under an inert atmosphere, e.g., a $N_2$ atmosphere, with slight heating to a temperature of about 35°–45° C. for several hours for improved yields. $H_2S$ is then bubbled through the solution and the solid product collected, by evaporation for example, while keeping the temperature below about 40° C. To this product dissolved in water, $R^2$-C(O)-SH (wherein $R^2$ is as described above) is added in a batchwise manner and the reaction maintained at a temperature no greater than about 5° C. This latter step reduces the amount of N-acetylation that occurs, which is undesirable because the N-acetylated products may not be as biologically compatible as the compounds of the present invention.

The method for protecting the sulfhydryl group is described herein for preparation of dipeptides of L-cysteine where the cysteine is C-terminal, although it can be applied to the preparation of other C-terminal cysteinyl peptides, by one of skill in the art.

Thus, the present invention provides a method for protecting sulfhydryl groups in a peptidyl compound comprising: using a 2-substituted-thiazolidine-4-carboxylate for coupling with phthaloyl-L-glutamic anhydride; and acylating the sulfhydryl group of C-terminal cysteinyl peptides with $R^2$-C(O)-SH, wherein $R^2$ is a $(C_1-C_{19})$alkyl group, a benzoyl group, a $(C_1-C6)$alkoxy group, or a $(C_3-C_{18})$ cycloalkyl group, at a temperature no greater than about 5° C.

Finally, the present invention provides a method for preparing a γ-glutamylcysteine compound comprising: coupling a 2-substituted-thiazolidine-4-carboxylate with a phthaloyl-L-glutamic anhydride; removing the phthaloyl protecting group with hydrazine; cleaving the thiazolidine ring with a divalent mercury salt at a temperature of about 35°–45° C. to generate a sulfhydryl group; and acylating the mercapto functional group with $R^2$-C(O)-SH, wherein $R^2$ is a $(C_1-C_{19})$alkyl group, a benzoyl group, a $(C_1-C_6)$alkoxy group, or a $(C_3-C_{18})$cycloalkyl group, at a temperature no greater than about 5° C.

Reasonable modifications and variations are possible from the foregoing disclosure without departing from either the spirit or scope of the present invention as defined by the claims. Objects and advantages of this invention will now be illustrated by the following examples, but the particular materials and amounts thereof recited in these examples, as well as other conditions and details, should not be construed to unduly limit this invention.

EXPERIMENTAL EXAMPLES $^1$H-NMR spectra were recorded at ambient temperature on either GE-300 or BRUKER AC-200 NMR spectrometers. Chemical shifts are reported as δ values (ppm). Mass spectra (FAB) were obtained on a KRATOS MS 25 mass spectrometer. For TLC analyses, ANALTECH silica gel GF and RPS-F plates were used. The solvent systems used for TLC were butanol:acetic acid:water (50:11:25) for normal phase, and acetonitrile:water (95:5 to 80:20) for reverse phase. The plates were visualized by spraying with ninhydrin solution and heating. Column chromatography was carried out using columns packed with octadecyl-functionalized silica gel (C-18 RPSG) (Aldrich Chemical Co.) KIESELGEL 60 (230–400 mesh), silica gel (EM Science) or BIOBEADS SM4 (Bio Rad, Inc.). Mercuric acetate was purchased from Fisher Scientific Co., thioacetic acid from Aldrich Chemical Co. or Sigma Chemical Co., and $H_2S$ (gas) from Matheson Gas Products.

Preparation of 3-(γ-L-Glutamyl)-2(R,S)-Methylthiazolidine-4(R)-Carboxylic Acid (1)

To a stirred suspension of 2(R,S)-methylthiazolidine-4(R)-carboxylic acid (8.51 g, 57.9 mmol) prepared according to Nagasawa et al., *J. Med. Chem.*, 27, 591 (1984), which is incorporated herein by reference, in dry $CH_3CN$ (100 mL) under a $N_2$ atmosphere was added bis-(trimethylsilyl) trifluoroacetamide (17.0 mL, 17.7 g, 68.7 mmol, obtained from Sigma Chemical Co., "BSTFA") and the mixture was heated under reflux for 1.25 hours. The solids dissolved within 10 minutes of heating. After cooling to room temperature, N-phthaloyl-L-glutamic anhydride (15.0 g, 58.0 mmol) prepared according to Elbefling et al., *Org. Prep. Proceed. Int.*, 11, 67 (1979), which is incorporated herein by reference, was added, followed by dry $CH_3CN$ (25 mL). After 5 days at room temperature the solvent was evaporated in vacuo. To the resultant pale yellow thick oil (41.1 g) were added with stirring under a $N_2$ atmosphere, 1.0M $Et_3N$ in $CH_3OH$ (220 mL) and 2.0M $NH_2NH_2.H_2O$ in 50% aqueous $CH_3OH$ (73 mL). After 2 days of stirring the solvent was evaporated in vacuo. The resultant thick, white, semisolid (51.8 g) was suspended in $H_2O$ (150 mL) and the solvent evaporated again to give 49.7 g of a thick, white oil. This was poured into warm $H_2O$ (350 mL) with swirling. The resultant precipitate of phthalhydrazide was removed by filtration and the filter cake was rinsed with $H_2O$ (approximately 100 mL). The combined filtrate was acidified to pH 3.5 with 1.0N HCl, whereupon more phthalhydrazide precipitated. This was removed by filtration, and the filtrate was evaporated in vacuo, keeping the temperature under 40° C., to give 35.8 g of a thick, pale yellow oil whose NMR spectrum showed the presence of much $Et_3N$ and some phthalhydrazide in addition to the desired product. The oil was, therefore, resuspended in $H_2O$ (75 mL), the mixture was stirred, and the additional solids that precipitated were removed by filtration. The filtrate was evaporated to incipient dryness in vacuo to give a thick oil (24.6 g).

The product thus obtained was purified by ion exchange chromatography. The column packed with 400 g of anion exchange resin (SBR nuclear grade, $OH^-$ form, Sigma Chemical Co., St. Louis, Mo.) was washed with $H_2O$ (3L), 1M acetic acid (2L), and $H_2O$ (4L) to convert it to the acetate form before charging with the product obtained above. The column was eluted with 0.5M acetic acid and 1.0M acetic acid to give 8.10 g (51% yield) of the titled compound as an off-white solid.

$^1$H NMR ($D_2O$): δ 1.52 and 1.63 (2d, J=6.3 Hz and J=6.5 Hz, 3H, $CH_3CH$), 2.2 (m, 2H, $CH_2CHNH_2$), 2.7 (m, 2H, $CH_2CO$), 3.4 (m, 2H, $CH_2S$), 3.8 (m, 1H, $CHNH_2$), 4.8 (m, 1H, $CHCO_2H$), 5.4 (m, 1H, $CHCH_3$). Mass spectrum (FAB): m/z 276 ($M^+$). Anal. ($C_{10}H_{16}N_2O_5S$) Calculated: C, 43.47; H, 5.84; N, 10.14. Found: C, 43.33; H, 5.79; N 10.12.

Preparation of 3-(γ-L-Glutamyl)-2(R,S)-Methylthiazolidine-4(R)-Carboxylic Acid Ethyl Eester (1a)

2(R,S)-Methylthiazolidine-4(R)-carboxylic acid ethyl ester was prepared by the condensation of L-cysteine ethyl ester with acetaldehyde. This involved neutralizing the hydrochloride salt of the former, condensation with acetaldehyde under nitrogen, extraction into ethyl acetate and purification of the product by distillation (b.p. 95°–103° C. at 0.6 mm Hg). To a stirred solution of 2(R,S)-methylthiazolidine-4(R)-carboxylic acid ethyl ester (9.12 g, 52.1 mmol) in dry $CH_3CN$ (90 mL) under a $N_2$ atmosphere was added bis-(trimethylsilyl)trifluoroacetamide (7.5 mL, 7.8 g, 30 mmol) and the mixture was heated under reflux for 50 minutes. After cooling to room temperature, N-phthaloyl-L-glutamic anhydride (13.8 g, 53.1 mmol) was added, followed by dry $CH_3CN$ (35 mL). After 3 days at room temperature, the solvent was evaporated in vacuo, keeping the temperature under 40° C. To the resultant orange oil (37.1 g) were added with stirring under a $N_2$ atmosphere, 1.0M $Et_3N$ in $CH_3OH$ (200 mL) and 2.0M $NH_2NH_2.H_2O$ in 50% aqueous $CH_3OH$ (70 mL). After 3 days of stirring, the solvent was evaporated in vacuo, the resultant thick paste was suspended in $H_2O$ (300 mL), and the solvent evaporated again to give 33.1 g of a dark yellow paste. This crude product was suspended in $H_2O$ (350 mL) and acidified to pH 3.0 with 1.0N HCl whereupon phthalhydrazide precipitated. This was removed by filtration, and the filtrate volume was reduced to approximately 200 mL by evaporation in vacuo when more phthalhydrazide precipitated. This was removed as above and the filtrate was evaporated in vacuo to incipient dryness to give 24.6 g of a thick orange oil.

The product thus obtained was purified by ion exchange chromatography using 140 g of cation exchange resin (AG 50WX4, $H^+$ form, Bio Rad Inc., Melville, N.Y.). The column was washed with $H_2O$ (1L) until the washings were colorless. It was eluted with 0.05N $NH_3$ to give 12.8 g (81% yield) of the titled compound as a light yellow solid.

$^1H$ NHR ($D_2O$): δ 1.36 (m, 3H, $CH_3CH_2$), 1.51 and 1.63 (2d, J=6.2 Hz and J=6.4 Hz, 3H, $CH_3CH$), 2.2 (m, 2H, $CH_2CHNH_2$), 2.7 (m, 2H, $CH_2CO$), 3.4 (m, 2H, $CH_2S$), 3.8 (m, 1H, $CHNH_2$), 4.2 (m, 2H, $CH_2CH_3$), 4.8 (m, 1H, $CHCO_2H$), 5.2 and 5.43 (m and q, J=6.4 Hz, 1H, $CHCH_3$). Mass spectrum (FAB): m/z 304 ($M^+$). Anal. ($C_{12}H_{20}N_2O_5S$) Calculated: C, 47.36; H, 6.62; N, 9.20. Found: C, 47.08; H, 6.75; N 8.94.

Preparation of
S-Acetyl-γ-L-Glutamyl-L-Cysteine (3)

3-(γ-L-Glutamyl)-2(R,S)-methylthiazolidine-4(R)-carboxylic acid prepared as described above (2.10 g, 7.60 mmol, Compound 1 in Scheme 1) in $H_2O$ (100 mL) was stirred under a $N_2$ atmosphere at about 40° C. Mercuric acetate (8.00 g, 25.1 mmol) in $H_2O$ (35 mL) was added under $N_2$ over 5 minutes. A heavy, white precipitate formed immediately. The mixture was stirred for 3 hours at 39°–44° C., then cooled to room temperature and $H_2S$ was bubbled through the stirred solution for 50 minutes. A black precipitate formed as soon as the $H_2S$ was introduced. Nitrogen was bubbled through the stirred mixture for 45 minutes to remove $H_2S$, after which time the solids were removed by filtration through CELITE. Nitrogen was again bubbled through the solution. After storage overnight in a refrigerator at a temperature of about 5° C., the solvent was evaporated in vacuo, keeping the temperature under 40° C. Addition of $H_2O$ (approximately 100 mL) followed by solvent evaporation was repeated twice to give 2.13 g of light pink solids. The NMR spectrum of the crude γ-L-glutamyl-L-cysteine (Compound 2 in Scheme 1) showed no starting material and a multiplet at δ 3.00 ppm assigned to the methylene group adjacent to SH.

The crude product was dissolved in $H_2O$ (120 mL) under $N_2$ and the solution cooled in an ice bath. Thioacetic acid (0.92 mL, 13 mmol) was added dropwise over 2 minutes and the mixture was shaken to dissolve all the reagent. The solution was then placed in a refrigerator and on the next day, a 1-mL aliquot was removed, diluted with $H_2O$, and the solvent evaporated in vacuo. NMR analysis showed about 80% starting material remaining based on the integration of the methylene multiplet at δ 2.93 in the starting material vs. the eight-line ABX pattern at about δ 3.5 ppm in the product. After 2 more days, NMR analysis as above showed 50–55% starting material. Additional thioacetic acid (0.55 mL, 7.8 mmol or 2 equivalents based on remaining starting material) was added. The, following day, NMR analysis as above showed about 35% starting material. The solution was concentrated to incipient dryness in vacuo, the residue diluted with $H_2O$ and the solvent evaporated again to remove acetic acid. This process was repeated twice to give 2.26 g solids which still contained 25–30% of starting material by NMR analysis. This thiolacetylation procedure was therefore repeated with 0.40-mL and 0.09-mL portions of thioacetic acid as above until the NMR analysis showed less than 5% starting material. About 5% of the N,S-bis-acetate had also formed, based on the ratio of the S-acetyl singlet at δ 2.36 ppm to the N-acetylated product singlet at γ 1.98 ppm.

The product thus obtained was purified by column chromatography using 185 g of silica gel. The column was washed with 2L of 0.001N aqueous HCl:1-propanol (1:10) and 500 mL of 0.001N aqueous HCl:1-propanol (1:20). The product was prepared for placing on the column by dissolving it in $H_2O$, adding 2.0 g of silica gel, removing the solvent, and then placing the coated silica gel on top of the column. The flask residues were scavenged by repeating this procedure with about 0.5 silica gel. The column was eluted with 0.001N aqueous HCl:1-propanol (1:20) and then 0.001N aqueous HCl:1-propanol (1:10). Representative ninhydrin-positive fractions were evaporated and the residues analyzed by NMR spectroscopy. The best fractions were combined and lyophilized. (The early fractions contained some pyroglutamic acid and up to about 10% of the bis-acetylated product.) The yield of pure 3 was 0.60 g (27%). Another 0.70 g (32% yield) of less pure product was also isolated.

$^1H$ NMR ($D_2O$): γ 2.14 (m, 2H, $CH_2CH$), 2.37 (s, 3H, $CH_3$), 2.43 (m, 2H, $COCH_2$), 3.19 (dd, J=14.2 Hz, J=7.3 Hz, 1H, SCH), 3.48 (dd, J=14.2 Hz, J=4.5 Hz, 1H, SCH), 3.82 (t, J=6.2 Hz, 1H, $CHNH_2$) 4.53 (dd, J=7.3 Hz, J=4.5 Hz, 1H, CHNH). Mass spectrum (FAB): m/z 292 ($M^+$).

The stability of compound 3 was evaluated in saline solution, as well as in buffered saline solution at physiological pH. Compound 3 was dissolved in 0.9% NaCl solution in $D_2O$, the sample placed in an NMR tube and the spectrum was monitored over time. No discernible change in the NMR spectrum was seen over the course of 1.5 months at room temperature, attesting to the high solution stability of this S-protected dipeptide precursor of glutathione. Compound 3 was then dissolved in 0.1 M phosphate buffer, the solution adjusted to a pH of 7.4 and NaCl was added to a concentration of 0.9%. There was no apparent change after 1–2 days. Only after 4 days was there any evidence of solvolysis of the S-acetyl group and after 1 month there was only a minor amount of a peak at δ 1.90, which corresponds to the resonance of sodium acetate (this peak represented only 8% of the height of the S-acetyl peak at δ 2.36). Thus, compound 3 represents a sulfhydryl protected, chemically stable dipeptide precursor of glutathione that can withstand pharmaceutical formulations without premature air oxidation.

Preparation of Ethyl S-Acetyl-γ-L-Glutamyl-L-Cysteinate (3a)

3-(γ-L-Glutamyl)-2(R,S)-methylthiazolidine-4(R)-carboxylic acid ethyl ester (Compound 1a in Scheme I) (3.08 g, 10.1 mmol) in $H_2O$ (50 mL) was stirred under a $N_2$ atmosphere at about 38° C. Mercuric acetate (10.0 g, 31.4 mmol) in $H_2O$ (50 mL) was added under $N_2$ over 2 minutes. A milky-white, foamy precipitate formed immediately. The mixture was stirred for 2.5 hours at 38°–41° C., then cooled to room temperature. $H_2S$ was then bubbled through the stirred solution for 45 minutes. A black precipitate formed as soon as the $H_2S$ was introduced. Nitrogen was bubbled through the stirred mixture for 30 minutes to remove $H_2S$, after which time the solids were removed by filtration through CELITE. Nitrogen was again bubbled through the filtrate, and after storage overnight in a refrigerator, the solvent was evaporated in vacuo, keeping the temperature under 40° C. Addition of $H_2O$ (approximately 75 mL), followed by solvent evaporation was repeated twice to give 2.16 g of pink solids. The NMR spectrum of the crude product showed no starting material and a multiplet at δ 3.00 ppm assigned to the methylene group adjacent to SH.

The crude γ-L-glutamyl-L-cysteine ethyl ester (Compound 2a in Scheme 1) was dissolved in $H_2O$ (100 mL) under $N_2$ and the solution cooled in an ice bath. Thioacetic acid (1.10 mL, 15.5 mmol) was added dropwise over 1 minute, and the mixture was shaken to dissolve all the reagent. The solution was then placed in a refrigerator and after 3 days the solvent was evaporated in vacuo, keeping the temperature under 40° C. Addition of $H_2O$ (approximately 75 mL) and solvent evaporation was repeated twice to give 2.43 g of light yellow solids. NMR analysis showed that about 30% starting material still remained, based on the integration of the methylene multiplet at δ3.0 ppm in the starting material vs. the eight-line ABX pattern at about δ 3.5 ppm in the product. The crude product was therefore dissolved in ice-cooled water (80 mL) under $N_2$, and thioacetic acid (0.4 mL, 5.6 mmol; 2.4 equivalents based on remaining starting material) was added and the reaction allowed to proceed further in the cold (refrigerated at a temperature of about 5° C.). NMR analysis of the product after 2 days showed about 10% starting material still remained. This thiolacetylation procedure was therefore repeated with 0.20 mL thioacetic acid, until the NMR analysis showed less than 5% starting material.

The product thus obtained was purified by column chromatography using 105 g of C-18 reverse-phase silica gel (RPSG). The column was washed with 500 mL each of $H_2O$ acetonitrile (1:3) and $H_2O$ acetonitrile (1:19). The crude product obtained above was prepared for placing on the column by dissolving it in $H_2O$, adding 1.1 g of RPSG, removing the solvent, and then placing the coated silica gel on top of the column. The flask residues were scavenged by repeating this procedure with 0.5 and then 0.2 g RPSG. The column was eluted with $H_2O$ :acetonitrile (1:19) and then $H_2O$:acetonitrile (1:9). The representative ninhydrin-positive fractions were collected, the solvent evaporated in vacuo, and the residue analyzed by NMR spectroscopy. The early fractions contained as much as 10% of the N,S-bis-acetylated product, while the later fractions showed decreased ester concentrations and some S-acetyl-γ-L-glutamyl-L-cysteine (Compound 3 in Scheme 1 ) plus some other unidentified material. The best fractions were combined and lyophilized to give 844 mg of light yellow solid (26% yield). The NMR spectrum showed a small doublet at about δ 1.6 ppm. This product was treated with decolorizing carbon, the mixture filtered, and the filtrate lyophilized again to give 491 mg of very pale pink solids whose NMR spectrum showed the almost complete disappearance of the doublet at δ 1.6 ppm. Another 1.2 g (37% yield) of less pure product was also isolated.

$^1H$ NMR ($D_2O$): δ 125 (t, J=7.1 Hz, 3H, $CH_2CH_3$), 2.10 (m, 2H, $CH_2CH$), 2.36 (s, 3H, $CH_3CO$), 2.45 (m, 2H, $COCH_2$), 3.26 (dd, J=14.3 Hz, J=7.1 Hz, 1H, SCH), 3.45 (dd, J=14.3 Hz, J=4.8 Hz, 1H, SCH), 3.81 (t, J=6.2 Hz, 1H, $CHNH_2$), 4.20 (q, J=7.1 Hz, 2H, $CH_2CH_3$), 4.65 (dd, J=7.1 Hz, J=4.9 Hz, 1H, CHNH). Mass spectrum (FAB): m/z 320 ($M^+$). Anal. ($C_{12}H_{20}N_2O_6S$) Calculated: C, 44.99; H, 6.29; N, 8.74. Found: C, 44.96; H, 6.15; N 8.76.

The stability of compound 3a was evaluated in saline solution. It was dissolved in 0.9% NaCl solution in $D_2O$, the sample placed in an NMR tube and the spectrum was monitored over time. No discernible change in the NMR spectrum was seen over the course of 1.5 months at room temperature, attesting to the high solution stability of this S-protected dipeptide precursor of glutathione. Thus, compound 3a represents a sulfhydryl protected, chemically stable dipeptide precursor of glutathione that can withstand pharmaceutical formulations without premature air oxidation.

Preparation of N,S-Bis-Acetyl-γ-L-Glutamyl-L-Cysteine

Crude γ-L-glutamyl-L-cysteine (1.59 g, 6.36 mmol) was dissolved in $H_2O$ (20 mL) under $N_2$ and the solution was stirred with ice bath cooling. A solution of $NaHCO_3$ (6.9 g, 82 mmol) in 80 mL $H_2O$ was added, followed by dropwise addition of acetic anhydride (3.6 mL, 3.9 g, 38 mmol) over 1 minute. After 2 minutes a test for free thiol was negative. The solution was acidified to pH 2.5–3 with 6N and then 1N HCl. Removal of the solvent afforded 8.3 g of white solids whose NMR spectrum showed the presence of both S-acetyl and N-acetyl groups. The solids were extracted with 4×50 mL portions of hot absolute ethanol to give 1.71 g of product which, along with 0.36 g from another run, was purified by flash chromatography using 100 g of silica gel. The column was eluted with n-propanol: 0.02N aq. HCl (95:5), followed by n-propanol:0.01N aq. HCl (90:10) to give 1.02 g of the titled compound.

$^1H$ NMR ($D_2O$) δ 2.0 (m, 2H, $CH_2CH_2CO$), 2.03 (s, 3H, $CH_3CONH$), 2.3 (m, 2H, $CH_2CO$), 2.37 (s, 3H, $CH_3COS$), 3.14 (dd, J=14.1 Hz, J=7.5 Hz, 1H, SCH), 3.48 (dd, J=14.1 Hz, J=4.4 Hz, 1H, SCH), 4.19 (dd, J=9.1 Hz, J=4.5 Hz, 1H, $CHCH_2CH_2$), 4.46 (dd, J=7.5 Hz, J=4.3 Hz, 1H, $CHCH_2S$).

Preparation of Ethyl N,S-Bis-Acetyl-γ-L-Glutamyl-L-Cysteinate

Crude γ-L-glutamyl-L-cysteine ethyl ester (1.31 g, 4.71 mmol) was acetylated in the same manner as for N,S-bis-acetyl-γ-L-glutamyl-L-cysteine, using 2.7 mL, (2.9 g, 28 mmol) of acetic anhydride. The 1.53 g of crude product obtained, along with 0.34 g from another run, was purified by column chromatography using 105 g of C-18 reverse-phase silica gel (RPSG). The column was washed with methanol, then with water. The column was eluted with $H_2O$, followed by $CH_3OH:H_2O$ (5:95), and finally with $CH_3OH:H_2O$ (10:90) to give 0.59 g of the titled compound.

$^1H$ NMR ($D_2O$) δ 1.25 (t, J=7.2 Hz, 3H, $CH_3CH_2$), 2.01 (s, 3H, $CH_3CONH$), 2.1 (m, 2H, $CH_2CH_2CO$), 2.34 (s, 3H, $CH_3COS$), 2.4 (m, 2H, $CH_2CO$), 3.21 (dd, J=14.2 Hz, J=7.4 Hz, 1H, SCH), 3.43 (dd, J=14.2 Hz, J=4.8 Hz, 1H, SCH), 4.18 (q, J=7.1 Hz, 2H, $CH_2CH_3$), 4.30 (dd, J=9.2 Hz, J=4.8 Hz, 1H, $CHCH_2CH_2$), 4.62 (dd, J=7.3 Hz, J=4.8 Hz, 1H, $CHCH_2S$); FAB/MS m/z 363 (MH+).

γ-Glutamylcysteine Prodrugs: Assay Method for Incorporation into Glutathione

Materials

Chemicals. The following reagents were obtained commercially: 2,4-dinitrofluorobenzene (FDNB), L-buthionine-(S,R)-sulfoximine (BSO), reduced and oxidized glutathione, γ-L-glutamyl-L-glutamic acid (γ-glu-glu), m-cresol purple, iodoacetic acid (IAA) and all amino acid standards (Sigma Chemical Company, St. Louis, Mo.); double-distilled perchloric acid (PCA) and bathophenanthrolinedisulfonic acid (BPDS) (G. F. Smith Chemicals, Columbus, Ohio); HPLC grade methanol (Fisher Scientific, Pittsburgh, Pa.); HPLC grade glacial acetic acid and sodium acetate (J. T. Baker, Phillipsburg, N.J.); MILLI-Q water (Millipore Corporation, Bedford, Mass.); and liquid [$^{14}$C(U)]-glycine, 55–100 mCi/mmol (American Radiolabeled Chemicals, Inc., St. Louis, Mo.).

Incubation medium. The culture medium consisted of MEM (Minimum Essential Media) from GIBCO/BRL, Grand Island, N.Y. (Cat. #380-2360), supplemented with the following constituents: MEM vitamins (GIBCO/BRL #320-1120), MEM amino acids (GIBCO/BRL #320-1130), MEM non-essential amino acids (GIBCO/BRL #320-1140), sodium pyruvate (GIBCO/BRL #320-1360), L-glutamine (GIBCO/BRL #320-5030) and L-ascorbic acid (GIBCO/BRL #850-3080); and gentamicin sulfate (0.1 mg/mL) (Elkins-Sinn, Inc., Cherry Hill, N.J.). Also added to all media was 3.0 mM BSO, which inhibits glutathione synthesis by eliminating virtually all of the γ-glutamylcysteine synthetase activity. The culture medium (pH 7.2–7.4) was then filtered with a 0.22 μm PVDF filter (Gelman Sciences, Ann Arbor, Mich.) into COSTAR six-well culture dishes. Total volume per well was 5.0 mL. This included media, test compound and isotope (10–15 μCi[$^{14}$C(U)]-glycine. Dishes were placed in a humidified, 5.0% $CO_2$/95.0% air incubator (Forma) at 34° C. to warm just prior to initiating lens culture. Final ionic strength was 305 mOs.

Methods

Human lenses. Human eyes were obtained from the Minnesota Lions Eye Bank at the University of Minnesota. Criteria for selection were: paired lenses only; total postmortem time of less than 24 hours; lenses were required to be in good condition with no visible damage or cataracts; donor age range was approximately 30–70 years. Upon arrival, lenses were removed using sterile technique and observed for damage and/or cataracts. Suitable lenses were placed in culture dishes, one lens per well, anterior side up. For each pair of lenses, one lens was placed in the 'control' medium (without dipeptide prodrug) and one lens was placed in the 'experimental' medium (with dipeptide prodrug). Lenses were then returned to the humidified incubator (5.0% $CO_2$/95.0% air) and incubated for 24 hours at 34° C. Following incubation, lenses were frozen immediately in liquid nitrogen and stored at −80° C. until preparation for analysis.

Rat lenses. Male Sprague-Dawley rats, 75–99 gram body weight, were anesthetized by injection of approximately 0.25 cc of a 1:1 mixture of ANASED (xylazine, 20 mg/mL) and KETASET (ketamine, 100 mg/mL) in the right rear thigh. When fully anesthetized (several minutes later), they were euthanized by injection of approximately 0.25 cc sodium pentobarbital solution (64.8 mg/mL) into the heart. Eyes were enucleated immediately after sacrifice and placed in a dish of media warmed to 34° C. Due to the uniformity of size, age and environmental conditions under which the rats were raised, no attempt was made to keep eyes in pairs. As lenses were excised, they were carefully freed of any attached zonules and placed in wells containing media, one lens per well, with half of the lenses being placed in 'control' medium and half in 'experimental' medium. Lenses were then returned to a humidified incubator (5.0% $CO_2$/95.0% air) and incubated for 24 hours at 34° C. Following incubation, lenses were frozen immediately in liquid nitrogen and stored at −80° C. until preparation for analysis.

Tissue Preparation. Human and rat lens extracts were prepared identically with the exception that human lenses were homogenized individually and due to their much smaller size, rat lenses were ground in pairs. Lenses were placed in a mortar chilled to −75° C., pulverized under liquid nitrogen, then added to 1.0 mL of frozen 10% PCA in 1.0 mM BPDS solution and slowly brought to 4° C. with stirring. The homogenates were then centrifuged at 4° C. at 15,000 x g for 40 minutes. The resulting extracts were derivatized using a modification of the Fariss and Reed method (Fariss et al., *Methods in Enzymology*, 143, 101–109 (1987)). In this modification, 500 μL aliquots of supernatants were added to foil-wrapped test tubes containing 0.05 mL of 3.0 mM γ-glu-gu (internal standard). The free thiols were immediately S-carboxymethylated by addition of 0.05 mL of 100 mM IAA and 0.48 mL of 2.0M KOH-2.4M $KHCO_3$, then mixed gently and incubated in the dark at room temperature for 10 minutes. The primary amines were derivatized by addition of 0.335 mL of 1.5% FDNB, vortexed thoroughly, capped and incubated in the dark at room temperature for 2 hours. Following this, 0.1 mL of 1.0M L-lysine was added to combine with unreacted FDNB, tubes were vortexed briefly and incubated overnight (16.0 hours) in the dark at room temperature. The final derivatized samples were centrifuged at room temperature at 1,000 x g for 10 minutes and filtered through a 0.22 μm PVDF filter just prior to HPLC analysis.

High performance liquid chromatography (HPLC). The HPLC system consisted of an IBM PS/2 computer as well as the following components from Beckman Instruments, Inc.: model 126 pump, model 166 UV detector, model 171 in-line radioisotope detector and a model 507 autosampler. A BROWNLEE 5 μm amino propyl (30×4.6 mm I.D.) guard column and a 5 μm 3-amino propyl (250×4.6 mm I.D.) analytical column (Chrom Tech, Inc., Apple Valley, Minn.) were used for the separation of thiols. Control of all HPLC components and all data analyses were done using the BECKMAN SYSTEM GOLD chromatography software. This software permits data emitting from the UV and radioisotope detectors to be collected simultaneously and also allows for extensive post-run analysis, including overlaying of chromatograms from the two detectors.

After a 100 μL injection of the derivatized lens samples, the column effluent was passed through the UV detector (absorption wavelength of 360 nm), then into the variable volume liquid scintillator flow cell of the radioisotope detector. Solvent A was 80% methanol; solvent B was 0.5M sodium acetate, glacial acetic acid (15% v/v) and methanol (64% v/v). The mobile phase was maintained at 85% solvent A and 15% solvent B for 3 minutes, then linearly increased to 99% solvent B over the next 10 minutes. After 12 minutes at 99% solvent B, the mobile phase was linearly decreased to 0% solvent B over two minutes and remained there for eight minutes. Solvent B was then linearly increased to the initial conditions of 15% over two minutes and remained there for the remaining eight minutes of the 45 minute run. Flow rate was maintained at 1.2 mL/min throughout.

Test Compounds. Five compounds were tested to determine their ability to increase glutathione in human lenses incubated in the presence of [$^{14}$C(U)]-glycine. The controls were contralateral lenses incubated without the test compounds. The compounds tested in human lenses as well as rat lenses were Compounds 3 (S-Ac-Glu-Cys) and 3a (S-Ac-Glu-CysOEt) shown in Scheme I, as well as Bis-Ac-Glu-CysOEt and Bis-Ac-Glu-Cys and Glu-Cys-OEt. Glu-Cys-OEt may be prepared according to the method described in Kitihara et al., PCT/WO Application 88 00,182 (Jul. 7, 1986). Controls in the rat lens study lacked the test compound but were not necessarily contralateral lenses. The final concentration of each compound in the media was 0.2–0.45 mM. A total of 68 human lenses and 28 rat lenses were incubated.

Data analysis. Data analysis involved comparing the percent of [$^{14}$C(U)]-glycine incorporated into [$^{14}$C]-glutathione in control versus experimental lenses. The results are shown in FIG. 1. These results show that in both human and rat lenses, three out of these five dipeptides increased [$^{14}$C]-glutathione when compared to control lenses lacking the indicated dipeptide. The percent increase ranged from about 7 percent to nearly 50 percent in the most effective dipeptide S-Ac-Glu-CysOEt (Compound 3a in Scheme I). In conjunction with two of the five dipeptides, the experimental lenses yielded 10–30% less [$^{14}$C]-glutathione than the control lenses. The least effective dipeptide was S-Ac-Glu-Cys (Compound 3 in Scheme I).

The complete disclosures of all patents, patent applications, and publications are incorporated herein by reference as if each were individually incorporated by reference. The invention has been described with reference to various specific and preferred embodiments and techniques. However, it should be understood that many variations and modifications may be made while remaining within the spirit and scope of the invention.

What is claimed is:

1. A compound of the formula:

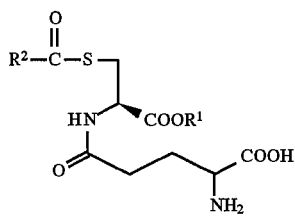

wherein $R^1$ is a ($C_1$-$C_{20}$)alkyl group, a ($C_6$-$C_2$)aryl group, or a ($C_3$-$C_{18}$)cycloalkyl group and $R^2$ is H or a ($C_1$-$C_{19}$)alkyl group, a ($C_6$-$C_{12}$)aryl group, a ($C_7$-$C_{13}$)arylalkoxy group, a ($C_1$-$C_6$)alkoxy group, a ($C_3$-$C_{18}$)cycloalkyl group, a

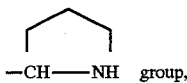

or a —CH($R^3$)NH$_2$ group wherein $R^3$ is a side chain of a natural amino acid.

2. The compound of claim 1 wherein $R^1$ is a ($C_1$-$C_6$)alkyl group and $R^2$ is a ($C_1$-$C_3$)alkyl group.

3. The compound of claim 2 wherein $R^1$ is an ethyl group and $R^2$ is a methyl group.

4. A pharmaceutical unit dosage form comprising an amount of a compound of the formula:

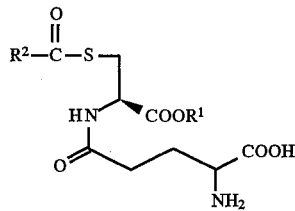

wherein $R^1$ is a ($C_1$-$C_{20}$)alkyl group, a ($C_6$-$C_{12}$)aryl group, or a ($C_3$-$C_{18}$)cycloalkyl group and $R^2$ is H or a ($C_1$-$C_{18}$)alkyl group, a ($C_6$-$C_{12}$)aryl group, a ($C_7$-$C_{13}$)arylalkoxy group, a ($C_1$-$C_6$)alkoxy group, a ($C_3$-$C_{18}$)cycloalkyl group, a

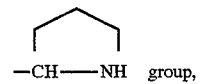

or a —CH($R^3$)NH$_2$ group wherein $R^3$ is a side chain of a natural amino acid, and the pharmaceutically acceptable salts thereof; in combination with a pharmaceutically acceptable carrier, wherein said amount is effective to increase the concentration of glutathione in tissue.

5. The pharmaceutical unit dosage form of claim 4 wherein $R^1$ is a ($C_1$-$C_6$)alkyl group.

6. The pharmaceutical unit dosage form of claim 5 wherein $R^1$ is an ethyl group.

7. The pharmaceutical unit dosage form of claim 5 wherein $R^2$ is a ($C_1$-$C_3$)alkyl group.

8. The pharmaceutical unit dosage form of claim 4 wherein $R^2$ is a ($C_1$-$C_3$)alkyl group.

9. The pharmaceutical unit dosage form of claim 8 wherein $R^2$ is a methyl group.

10. A method of enhancing the concentration of glutathione in tissues comprising administering an effective amount of a compound of the formula:

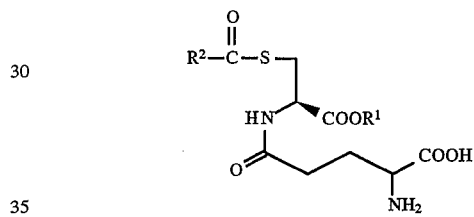

wherein $R^1$ is a ($C_1$-$C_{20}$)alkyl group, a ($C_6$-$C_{12}$)aryl group, or a ($C_3$-$C_{18}$)cycloalkyl group and $R^2$ is H or a ($C_1$-$C_{19}$)alkyl group, a ($C_6$-$C_{12}$)aryl group, a ($C_7$-$C_{13}$)arylalkoxy group, a ($C_1$-$C_6$)alkoxy group, a ($C_3$-$C_{18}$)cycloalkyl group, a

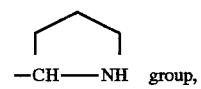

or a —CH($R^3$)NH$_2$ group wherein $R^3$ is a side chain of a natural amino acid, and the pharmaceutically acceptable salts thereof; in combination with a pharmaceutically acceptable carrier, wherein said amount is effective to increase the concentration of glutathione in tissue.

11. The method of claim 10 wherein $R^1$ is a ($C_1$-$C_6$)alkyl group.

12. The method of claim 11 wherein $R^1$ is an ethyl group.

13. The method of claim 11 wherein $R^2$ is a ($C_1$-$C_3$)alkyl group.

14. The method of claim 10 wherein $R^2$ is a ($C_1$-$C_3$)alkyl group.

15. The method of claim 11 wherein $R^2$ is a methyl group.

* * * * *

UNITED STATES PATENT AND TRADEMARK OFFICE
CERTIFICATE OF CORRECTION

PATENT NO. : 5,624,955
DATED : April 29, 1997
INVENTOR(S) : H.T. Nagasawa, W.B. Rathbun, and J.F. Cohen It is certified that error appears in the above-identified patent and that said Letters Patent is hereby corrected as shown below:

In the Abstract, after the second chemical figure, delete one occurrence of "group,";
Col. 9, line 18, delete "$(C_1-C6)$ and insert --$(C_1-C_6)$--;
Col. 11, line 65, delete "The," and insert --The--;
Col. 12, line 29, delete "γ" and insert --δ--;
Col. 13, line 53, delete "carbon,," and insert "--carbon,--;
Col. 17, line 33, delete "$(C_6-C_2)$" and insert --$(C_6-C_{12})$--; and
Col. 17, line 62, delete "$(C_1-C_{18})$alkyl" and insert --$(C_1-C_{19})$alkyl--.

Signed and Sealed this

Sixteenth Day of December, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.        : 5,624,955                                          Page 1 of 1
APPLICATION NO.   : 08/433809
DATED             : April 29, 1997
INVENTOR(S)       : H.T. Nagasawa, W.B. Rathbun and J.F. Cohen It is certified that error appears in the above-identified patent and that said Letters Patent is hereby corrected as shown below:

Column 1, after title, insert:

--Government Funding
This work was supported by the U.S. Department of Veterans Affairs and the Federal Government has certain rights in this invention.--

Signed and Sealed this

Fifteenth Day of August, 2006

JON W. DUDAS
*Director of the United States Patent and Trademark Office*